United States Patent [19]

Mönch

[11] Patent Number: 4,730,729
[45] Date of Patent: Mar. 15, 1988

[54] CONTAINER FOR ENDOSCOPES AND SPARE PARTS

[76] Inventor: Harry Mönch, Schwabstrasse 4, 7134 Knittlingen, Fed. Rep. of Germany

[21] Appl. No.: 783,183

[22] Filed: Oct. 2, 1985

[30] Foreign Application Priority Data

Oct. 5, 1984 [DE] Fed. Rep. of Germany ....... 3436489

[51] Int. Cl.[4] ................................................ A61C 2/26
[52] U.S. Cl. ................................... 206/370; 206/363; 206/438; 422/300; 422/310
[58] Field of Search ............... 206/305, 363, 370, 438, 206/439, 443, 464, 465, 477, 485, 497, 562, 563, 564, 569, 828; 422/300, 310

[56] References Cited

U.S. PATENT DOCUMENTS

| | | | |
|---|---|---|---|
| 3,132,909 | 5/1964 | Josefson | 206/305 |
| 3,416,250 | 12/1968 | Schweers | 206/316 |
| 3,489,268 | 1/1970 | Meierhoefer | 206/497 |
| 3,696,920 | 10/1972 | Lahay | 206/370 |
| 3,890,096 | 6/1975 | Nichol et al. | 206/564 |
| 3,983,996 | 10/1976 | Hendren, III | 206/363 |
| 4,135,868 | 1/1979 | Schainholz | 206/438 |
| 4,413,731 | 11/1983 | Weideman | 206/443 |
| 4,466,552 | 8/1984 | Butterworth et al. | 206/439 |

FOREIGN PATENT DOCUMENTS

| | | | |
|---|---|---|---|
| 2730895 | 1/1979 | Fed. Rep. of Germany | 206/443 |
| 2839219 | 3/1980 | Fed. Rep. of Germany | 206/439 |
| 951176 | 10/1949 | France | 206/305 |

Primary Examiner—Stephen Marcus
Assistant Examiner—David Fidei

[57] ABSTRACT

The container for dispatching, disinfecting, sterilizing and storing a variety of instruments such as endoscopes and parts therefore is so constructed that selectible bearing elements comprising pads may be utilized releasably and exchangeably in the container tray and/or lid, which fixedly support one or more side-by-side instruments in the container. By fitting bearing elements of different sizes a wide variety of different instruments can be accommodated.

12 Claims, 19 Drawing Figures

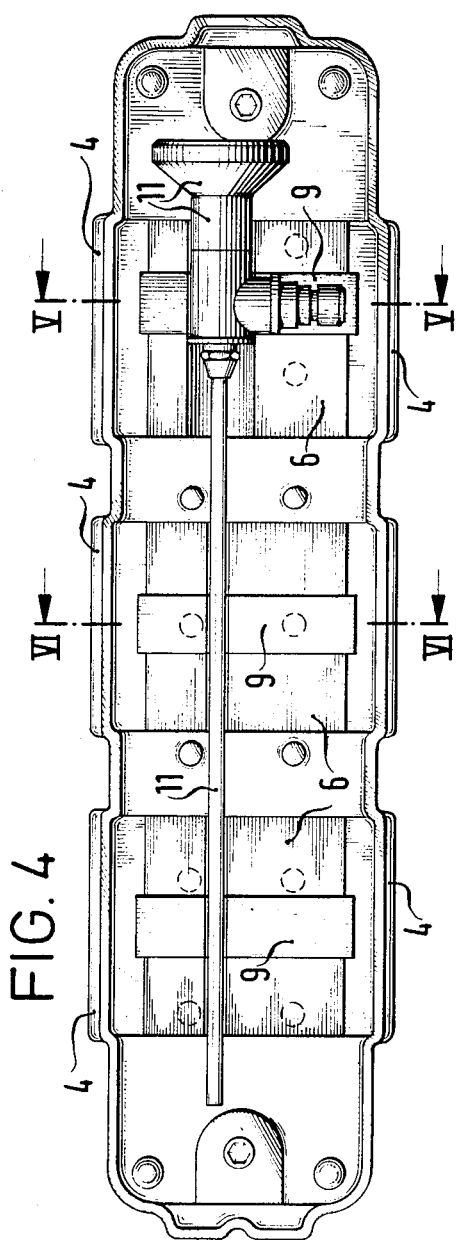
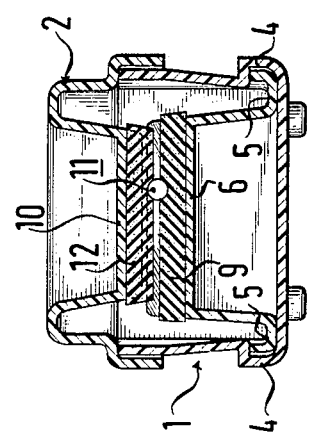
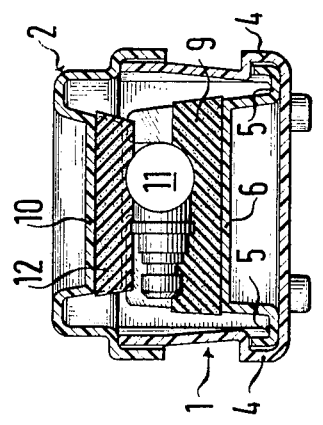

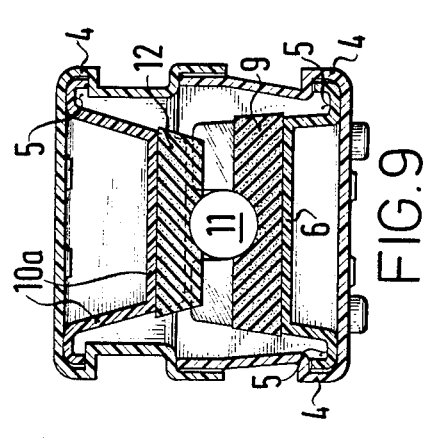
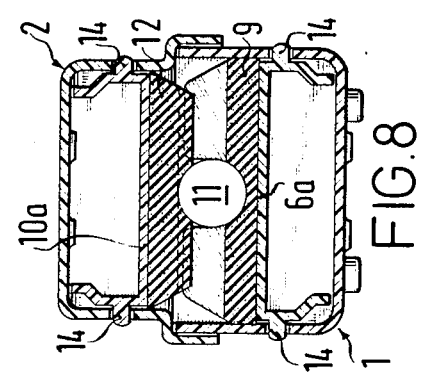
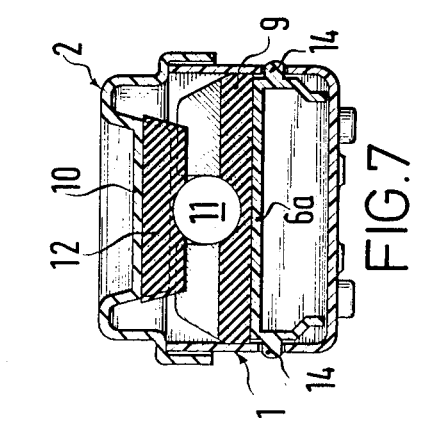
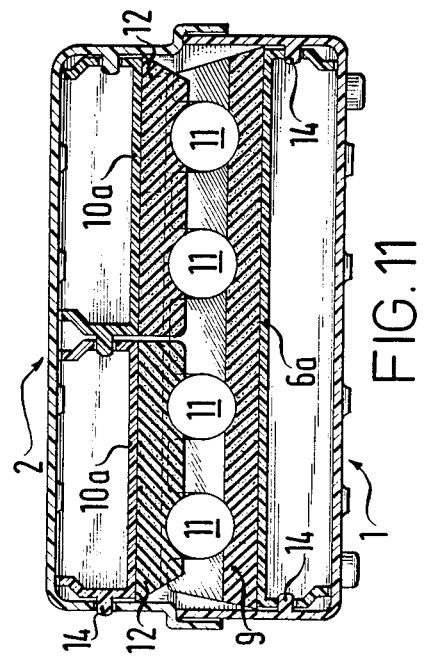
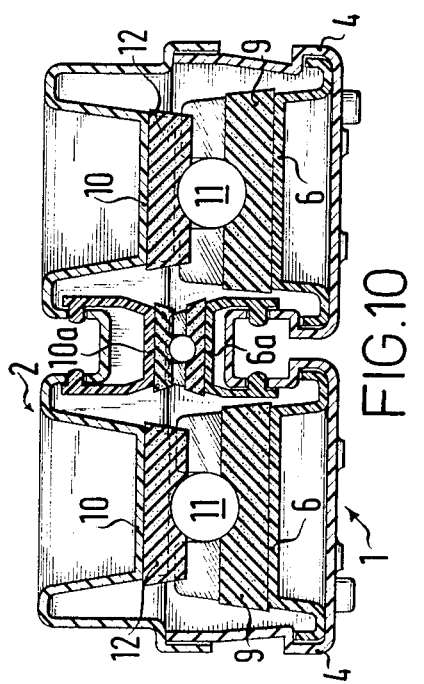

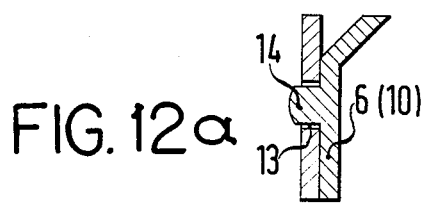 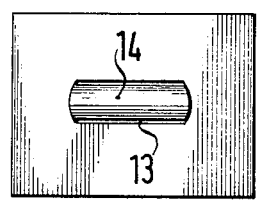
FIG. 12a　　　　　FIG. 12
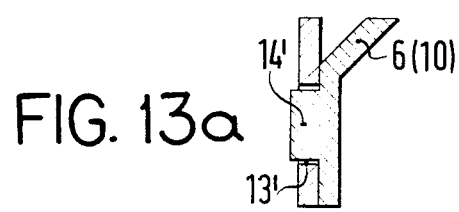 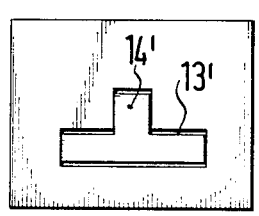
FIG. 13a　　　　　FIG. 13
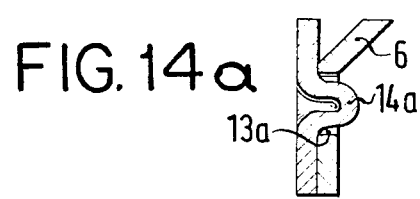 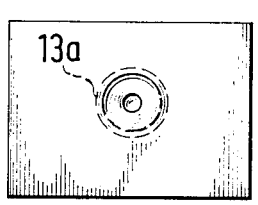
FIG. 14a　　　　　FIG. 14
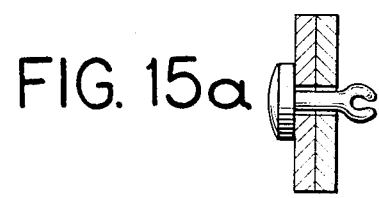 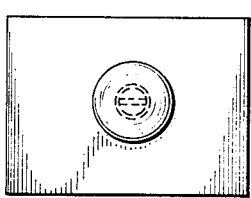
FIG. 15a　　　　　FIG. 15

4,730,729

CONTAINER FOR ENDOSCOPES AND SPARE PARTS

BACKGROUND OF THE INVENTION

The invention relates to a container comprising an elongated tray with a lid which may be placed thereon and fastened by means of clamping shackles or the like, for dispatching, sterilising and storage of medical apparatus items such as endoscopes and transducers which may be immobilised in their position by means of bearing elements situated opposite to each other in the container.

DESCRIPTION OF THE PRIOR ART

German specification No. 3414679 discloses a container in the form of a tray closable by means of a lid, which may be utilised for dispatching, disinfecting, sterilising and storing ultrasonic transducers. The container immobilises the transducer and accessories or spare parts.

SUMMARY OF THE INVENTION

It is an object of the invention to devise a container of a particular size for the instruments of approximately equal overall dimensions divided into a limited number of groups, so that single or several instruments may be fixedly housed separately or jointly in a container for dispatch, sterilisation, disinfection and storage.

According to the invention, this object is accomplished in that in the case of a container of the type referred to in the foregoing, which may be of different sizes, the elements fixedly supporting an instrument or several instruments and/or accessory or spare parts placed side-by-side, are releasable and exchangeable for adaptation to the instruments or accessories which is or are to be housed, in the tray at least. In this connection, the procedure advantageously applied to exchange the bearing elements is such that they engage with elastically outwardly springy projections of their sides into recesses of the container sidewalls, or that the reverse procedure is applied. In particular, it is possible to proceed such that the recesses of the container sidewalls form internal grooves in the form of lateral hollow projections or extensions at the bottom or top edges, wherein engage corresponding lateral projections of the cross-sectionally advantageously U-shaped bearing elements. It is also possible for the lateral surfaces of the U-shaped bearing elements to engage with projections in recesses of at least the tray sidewalls, or vice versa.

The invention and further advantages thereof are described in the following in respect of specific embodiments with reference to the drawings.

BRIEF DESCRIPTION OF THE DRAWINGS

FIG. 4 shows a plan view of the bottom container tray with an optical system of an endoscope stowed therein;

FIGS. 5 and 6 show two cross-sections along the lines V to V and VI to VI of FIG. 4, showing the lid in position;

FIGS. 7, 8 and 9 show cross-sections comprising parts modified as compared to FIGS. 5 and 6;

FIGS. 10 and 11 show two cross-sections through containers of greater width,

FIGS. 12 to 15 are side views of the recesses of the container sidewalls, and the projections in engagement, and FIGS. 12a to 15a are cross sectional views of the engaged recesses and projections of FIGS. 12-15.

DETAILED DESCRIPTION OF THE PREFERRED EMBODIMENTS

The container, advantageously produced from plastic material for reception of endoscopes of varying kinds, and of accessories of spares if applicable, comprises an elongated bottom tray 1 which has a lid 2 releasable connected to it by springy clamping shackles 3 which engage in known manner with projections over a peripheral step of the lid.

Figure 3:
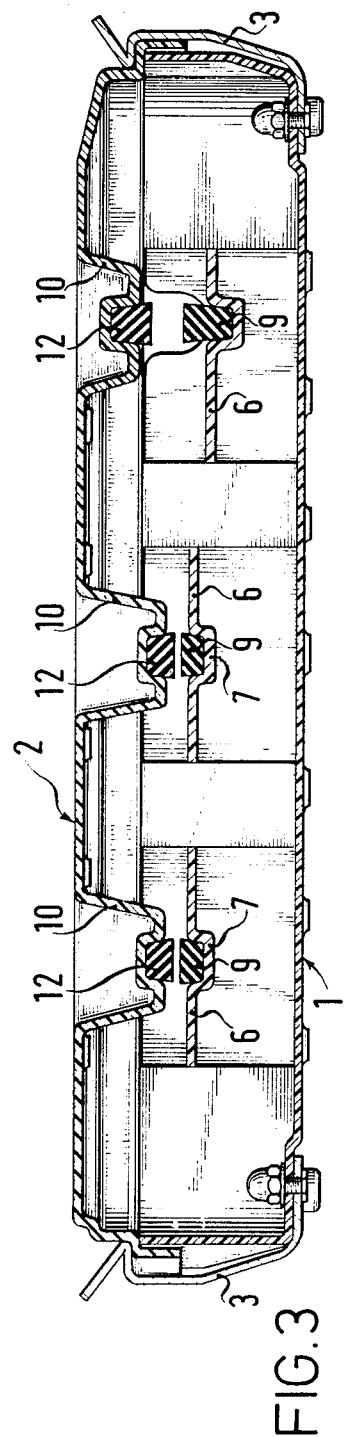
FIG. 3 shows a cross-section on the line III—III of FIG. 2.
Figure 1:
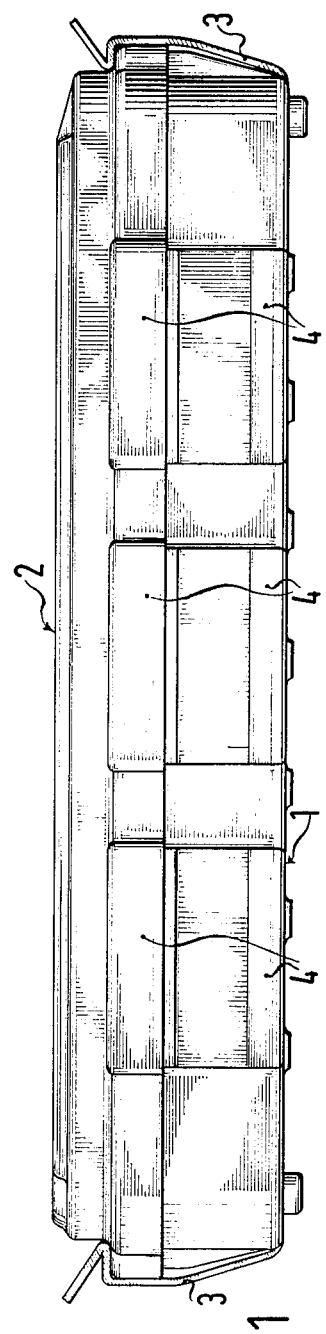
FIG. 1 shows a side elevation of a container in accordance with the invention.
Figure 2:
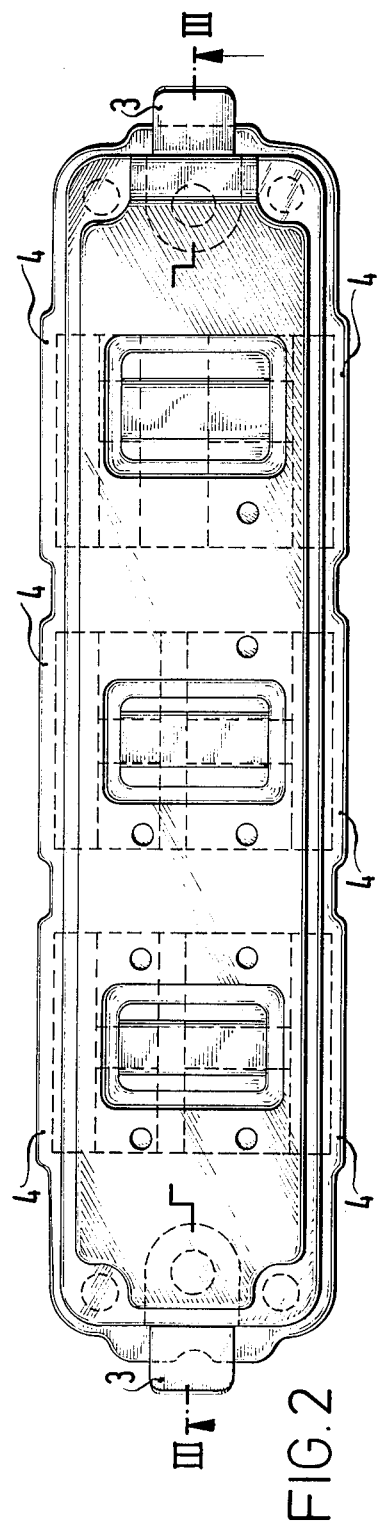
FIG. 2 shows a plan view of the container of FIG. 1.

To enable instruments of various different kinds, e.g. an optical system of an endoscope 11 as shown in FIG. 4, to be stowed fixedly in the container for dispatch, disinfection or sterilisation and storage, the tray 1 is provided according to FIGS. 1 to 6 with lateral hollow extensions 4, which are close to the base edge and form inwardly open grooves which are engaged in a resilient manner by lateral sectional projections 5 of bearing elements 6 of identical or dissimilar height and width. These bearing elements 6 formed which are from plastic material are advantageously produced with a U-shaped with an upwardly directed web which is provided with a transverse groove 7 for reception of a resilient pad 9, which is preferably being a pad of expanded material (e.g. foam rubber or expanded polystyrene) of different cross-sections for adaptation to the instruments. The bearing elements 6, 9 are confronted by corresponding supports 10 of the lid with pads 12 inset in grooves, which are fixed parts of the lid 2 according to FIGS. 1 to 6, but may also be releasable bearing elements 10a according to FIGS. 8,9 and 11.

A supportive adaptation to different instruments is possible by selection of the shape of the bearing elements 6,6a,10,10a as well as of the pads 9 and 12.

Instead of the engagement of the lateral projections 5 of the supports 6 into the grooves formed by the hollow extensions 4, it is also possible to provide the sidewalls of the tray 1 and the lid 2 with contoured perforations 13 which engage the correspondingly contoured projections 14 of the supports 6a and 10a which are stabilised thereby (FIGS. 7 and 8). This engagement is illustrated in enlarged form in FIGS. 12 and 13. It is also possible to do the opposite, as shown by FIG. 14, according to which a projection 13a of the container sidewalls engages resiliently in a contoured perforation 14a of the bearing element 6 or 10.

According to the example of FIG. 11, the width of the container is chosen greater to allow a receiving of several instruments 11 one beside another, the lower bearing element 6a being joined to the sidewalls according to FIG. 14, whereas the support in the lid comprises two bearing elements 10a which are connected to each other and to the lid sidewalls by means of projections and excisions according to one of the FIGS. 12 to 14.

Finally, the tray 1 and the lid 2 may according to FIG. 10 be provided with different side-by-side supports 6, 6a and 10,10a, which may again be placed in resilient engagement with the container sidewalls and partitions, or to which end the supports 10 of the lid may also be fixed parts of the lid 2.

Thanks to the shape of the container comprising a tray and a lid, and to its size, as well as to the releasable and exchangeable supports, containers may be utilised for dispatching, and stacked one above another, for storing instruments of the most different kinds of embodiment. The tray and/or the lid as well, are provided with perforations so that the instruments inserted may be disinfected with the container in liquids or that a sterilisation may also be performed in autoclaves by penetration of sterilising gas into the container.

I claim:

1. A container for storing, dispatching and sterilizing medical instruments comprising an elongated tray having lateral side walls; a lid fitting over and closing said tray; releasable clamps for securing said lid to said tray; a plurality of substantially inverted U-shape bearing elements being releasably secured in said tray at spaced intervals along its length, each of said elements having a pair of resilient side-arms with formations thereon engaging corresponding formations in said lateral side walls of the tray; a groove formed in an upper surface of each bearing element facing said lid and extending transversely to the longitudinal direction of the container, each groove accommodating a pad of resilient material to bear against said instrument; and a complementary bearing element in said lid, opposite each bearing element in said tray, each of the bearing elements in the lid having a transverse groove therein accommodating a pad of resilient material cooperating with the pad of the opposite bearing element of the tray to hold said instrument, the bearing elements of at least said tray being interchangeable with other such elements of different dimensions to enable different instruments to be accommodated in said container.

2. A container according to claim 1, wherein the formation on each of the elements comprises a lateral projection on each of the side-arms of the element and said formation on the lateral side walls comprises a recess for each projection.

3. A container according to claim 2, wherein each recess is a hollow extension molded in the side wall of the tray.

4. A container according to claim 2, wherein each recess is a slot formed in the side wall of the tray.

5. A container according to claim 1, wherein each formation of the tray is an inward projection and each formation of the side-arms is a recess for receiving the inward projection.

6. A container according to claim 1, wherein the complementary bearing elements of the lid are removable.

7. A rigid container for dispatching, sterilizing and storing of medical instruments, said container containing an elongated tray having side walls; a lid being connected to the tray; and said tray and lid being provided with projecting opposing and interchangeable supports between which the instruments are placed and fixed, the supports for at least the tray being directed transverse to the elongated direction of the tray and comprising resilient U-shaped bearing elements having a pair of resilient side-arms, said side-arms and side walls of the tray having coacting pairs of laterally extending projections and recesses for releasably mounting the bearing element in the tray.

8. A container according to claim 7, wherein the coacting recesses are formed in the side-arms of the bearing elements and the lateral projections are inwardly extending projections on the side walls of the tray.

9. A container according to claim 7, wherein the bearing supports of the lid are rigidly secured therein.

10. A container according to claim 7, wherein the bearing elements in the lid are also removably mounted therein.

11. A container according to claim 7, wherein the projections are outwardly extending projections on the side-arms of the bearing elements and the recesses are on the side walls of the lid.

12. A rigid container according to claim 11, wherein the recesses are molded into the side walls of the tray.

* * * * *